United States Patent [19]

Kim

[11] Patent Number: 5,433,728
[45] Date of Patent: Jul. 18, 1995

[54] SURGICAL NEEDLE

[76] Inventor: Il G. Kim, Laurel Hill, Box 15A, R.R. #1, Hughesville, Pa. 17737

[21] Appl. No.: 205,199

[22] Filed: Mar. 2, 1994

[51] Int. Cl.⁶ .............................................. A61B 17/00
[52] U.S. Cl. ................................. 606/223; 606/222; 606/224; 606/205; 606/207
[58] Field of Search ............... 606/139, 144, 147, 148, 606/151, 205, 207, 222-227; 223/102, 104; 163/5; 289/16; 112/222

[56] References Cited

U.S. PATENT DOCUMENTS

| 2,811,157 | 10/1957 | Kurtz et al. | |
| 2,811,971 | 11/1957 | Scott | |
| 3,608,095 | 3/1970 | Barry | |
| 4,373,530 | 2/1983 | Kilejian | 606/145 |
| 4,524,771 | 6/1985 | McGregor et al. | |
| 4,760,848 | 8/1988 | Hasson | 606/222 |
| 5,059,207 | 10/1991 | Shah | |
| 5,222,962 | 6/1993 | Burkhart | 606/148 |

FOREIGN PATENT DOCUMENTS

| 4114204 | 11/1992 | Germany | 606/148 |
| 1572613 | 6/1990 | Russian Federation | 606/223 |
| 876354 | 8/1961 | United Kingdom | 223/102 |

Primary Examiner—Stephen C. Pellegrino
Assistant Examiner—Jeffrey A. Schmidt
Attorney, Agent, or Firm—Thomas R. Shaffer

[57] ABSTRACT

A generally sickle shaped needle having a short shank is disclosed. An optional perpendicularly aligned grooved needle holder may be utilized in combination with the needle to rapidly close deeply lying trocared fascial wounds to prevent sequela and hernia formation after laparascopic surgery.

16 Claims, 2 Drawing Sheets

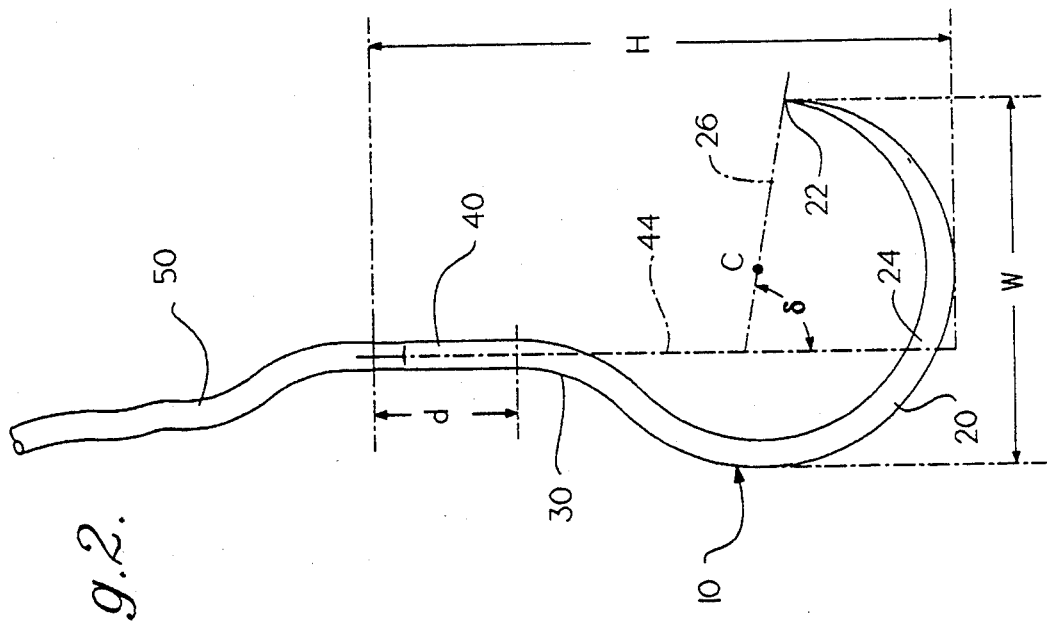
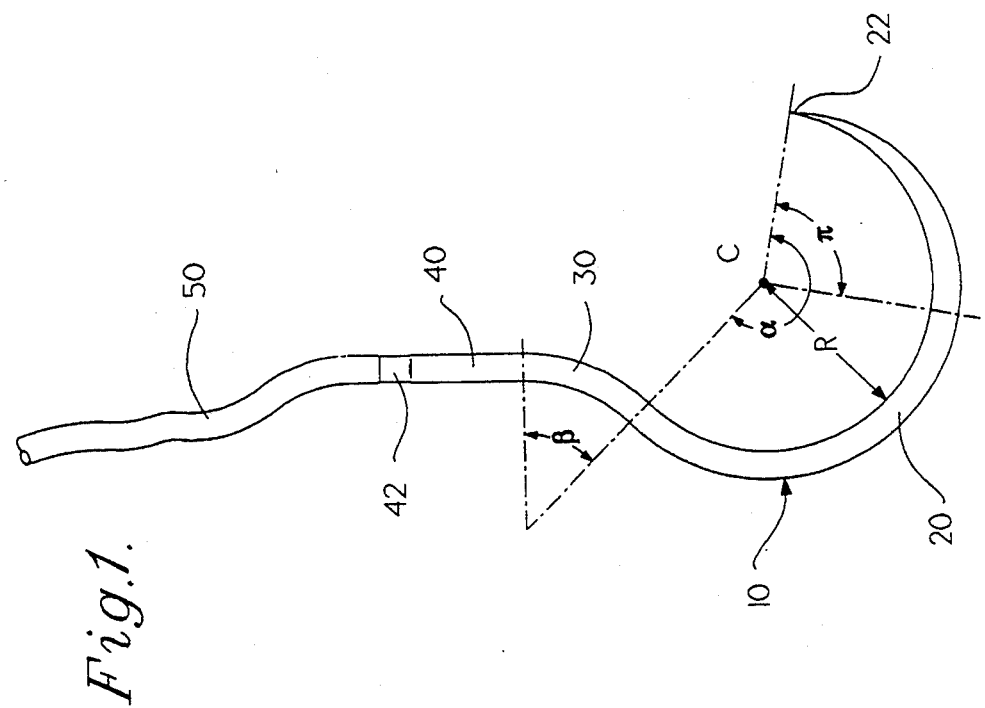

SURGICAL NEEDLE

BACKGROUND OF THE INVENTION

1. Field of the Invention

The present invention relates to a new and improved surgical needle. More specifically, it relates to an inexpensive, simply designed sickle shaped needle having a short shank utilized to rapidly close deeply lying trocared fascial wounds after laparascopic surgery. An optional modified needle holder is also disclosed.

2. Description of the Prior Art

A variety of surgical needles have been proposed in the past. Typically, prior needles have been formed of wire into a circular arc ranging from ¼ to ⅜ of a circle and having a sharpened point or edge for cutting. A variety of specialized needles utilized for a particular purpose have been proposed in a variety of other shapes. Examples of such needles are described below.

In R. J. Barry, U.S. Pat. No. 3,608,095, a needle is disclosed for use on the surface of the head for hair transplants. The needle has a curved or hook-like pointed terminal 21 adapted to penetrate the scalp and a long shank portion 20 to which a Teflon tube attachment 22 is provided. Because of the long shank, it would be completely impossible to suture deeply located fascial closures which are located below the subcutaneous fatty layer with such a needle. Further, the size and shape of the needle will not fit through the small laparascopic puncture wound into the abdomen.

In L. D. Kurtz et al, U.S. Pat. No. 2,811,157, a needle is shown in the drawings which bears a superficial resemblance to the shape of the needle of the present invention. The shape of the needle is described merely as being of the well-known variety and may be straight or curved with the suture fixed within the end of the needle. The needle has a cutting edge designed to penetrate the tissue easily and may have a non-cutting portion used for more delicate tissue. The invention is mainly used for minimal traumatic surgeries. It could not, however, be effectively used to suture deeply located fascia below the subcutaneous fatty layer through a 10 mm. trocared opening in the abdominal wall because of the shape disclosed would result in an increased risk that the point of the needle would puncture tissue during insertion.

In J. R. Scott, U.S. Pat. No. 2,811,971, multiple needles are hooked to the skin, opposite one another to close a wound at the surface of the skin. Each needle has a handle which is taped fast to the skin. The needles are left in place until the wound is healed. Because such needles have long handle style shanks, they would be completely unsuitable for suturing fascia which is located below the subcutaneous fatty layer. The goose neck of the needle and the long handle would clearly prevent rotation of the needle and removal from the fascia.

In Shah, U.S. Pat. No. 5,059,207, a variety of V and U shape needles are disclosed. Because of their shape, it would be extremely difficult to rotate needles out of one end of the skin to the opposite side of the skin end and would be especially difficult to suture multiple layers at one time.

These needles use a blind approach and there is a significant risk involved of inadvertently catching and puncturing the bowels, stomach, omentum, or internal organs. Although a blunt probe is used, there is still risk involved with the process disclosed because of the uncertainty of the depth of needle penetration and length of needles on different thicknesses of each individual abdominal wall, especially on the obese patient. Further, it is difficult to pass the needle and rotate it to bring it out of the skin using the V or U shape needles on different thicknesses of the abdominal wall at one time. Therefore, this invention's range of skin entrance by needle on either side is 1.0 cm. to 5 cm. of distance depending on the abdominal wall thickness of the tissue. This is a tremendous distance on a skin puncture and suggests that some rotating difficulty of the needle may be encountered on the overweight patient.

Still further, when suturing multiple layers of the abdominal wall, the skin can become inverted and wrinkled. Also, a great amount of pressure is exerted on the skin surface from the tied knots which prevent separation of the deep layers. Sutures must remain in place to heal deep layer of the fascia, at least three weeks. During this time, undesirable scar formation may occur at the knot area and puncture site.

Laparascopic surgery usually involves four puncture wounds in the abdominal wall. Using Shah's needle would create even more puncture wounds resulting in needless undesirable scar formation. Most laparascopic surgeons utilize subdermal dissolving skin sutures for cosmetic reasons.

In McGregor et al, U.S. Pat. No. 4,524,771, a needle is disclosed strictly for corneal transplants of the eye under a microscope. It has a sharp, hook-type tip and a tapered shaft to pick up small bits of delicate eye tissue. The needle is fine and small and is used for surface work; not heavy tissue in the deep abdominal wall.

The needle has a fish-hook type needle with a mildly curved end. The radius of curvature is from 0.040 inches to 0.075. The length curvature is from 0.063 inches to 0.105 inches. The blunt end of the needle has a radius of curvature from 0.081 inches to 0.015 inches. It has a gentle curvature and can therefore smoothly penetrate delicate tissue by circular motion for surface work. This fish-hook type needle clearly does not have sufficient curvature and does not have a heavy enough gauge needle to suture deeply located fascia in the abdominal wall through a 10 mm. puncture wound; especially on the overweight patient. This type of needle would likely break if it were to be used to encircle heavy tissue. Still further, the curved end of the needle makes it difficult to grasp and stabilize the needle while suturing deep tissue, unless surface work is being sutured.

Thus, there remains a need for an inexpensive and effective surgical needle which may be utilized to rapidly close deeply lying trocared fascial wounds after laparascopic surgery.

SUMMARY OF THE INVENTION

With the recent explosion of the new minimal invasive surgery, surgeons are facing the problem of closing deeply located fascia. More advanced minimal access surgery has larger trocar wounds such as 10.5, 11.5, and 15 mm. size in diameters. These types of defects caused by trocar wounds are difficult to close through small openings during the course of laparascopic surgery.

It is generally considered advisable to suture and close abdominal fascia trocar wounds having a diameter of 10 mm. or larger in order to prevent future undesirable sequela and hernia development. Such fascial defects at the shallow umbilical port are easy to close using regular suture needles. However, it is extremely difficult to close the thick part of the abdominal fascial defect through a deep and narrow trocar wound, especially on the overweight patient.

Thus the present invention provides a unique and simply designed generally sickle shaped needle which is preferably used in an improved needle holder to alleviate the difficulty encountered in closing deeply located fascial defects through trocared openings. The improved needle holder has a perpendicular groove on the center of the gripping faces of needle holder tip to prevent movement of the needle during suturing of the fascia.

The needle of the present invention includes an arcuate body segment which curves in a concave manner around a center point. The body segment has a sharp point at its terminal end and preferably has a tapered end which tapers gradually to the sharp point over an arcuate distance $\pi$ of approximately 90 degrees. The needle also includes a straight shank segment having a suture attached at a terminal end thereof. The shank segment is relatively short, having a length not substantially greater than said internal radius of curvature of the body segment. Finally, the needle includes a neck segment positioned intermediate and connecting together said body segment and said shank segment. The neck segment curves in a convex manner relative to the body segment and is attached to the body segment at an angle such that an extension of an axial centerline of the shank segment intersects the body segment in a central portion thereof. Preferably, the extension of the centerline of the shank segment intersects an extension of a line passing through the center point and sharp point at an angle $\delta$ between approximately 45 degrees and 90 degrees with a preferred angle of approximately 80 degrees.

Preferably, the body segment extends an arcuate distance $\alpha$ of between approximately 180 degrees to 230 degrees with a preferred arcuate distance of approximately 215 degrees. The internal radius of curvature of the body segment is preferably between approximately 4 millimeters and 5 millimeters in length with the preferred length being approximately 4.5 millimeters. Preferably, the shank segment has a length between approximately 2.5 millimeters and 4 millimeters with the preferred length being approximately 3 millimeters.

A surgical needle of the present invention preferably has an overall length of approximately 14 millimeters and an overall width of approximately 10 millimeters and is preferably formed of wire of generally circular cross section having a diameter of approximately 1 millimeter.

In a preferred form the invention includes both a needle as described above which is utilized in combination with an improved needle holding means. The needle holding means is generally in the form of surgical needle holders which have a pair of needle nosed gripping faces at one end adapted to be moved relatively closer together and grip said shank segment of said surgical needle. Each of the gripping faces have a longitudinal groove formed therein to receive and properly position the shank segment in axial alignment with the grooves. Preferably, the shank segment of the needle has a cross sectional diameter greater than the width of said grooves and the grooves have an axial length of approximately 10 millimeters.

The needle of the present invention has a certain curvature as described herein with a short shank which may be securely held in the grooved needle holder in the desired orientation. With this arrangement, the needle can reach any depth of tissue through a narrow (10 mm.) opening of the abdominal wound and is especially well suited for use on very obese patients.

BRIEF DESCRIPTION OF THE DRAWINGS

FIG. 1 is a side elevational view of a surgical needle according to the present invention.

FIG. 2 is a side elevational view of the surgical needle of FIG. 1 showing additional features of the needle.

DETAILED DESCRIPTION OF THE PREFERRED EMBODIMENTS

Figure 3:
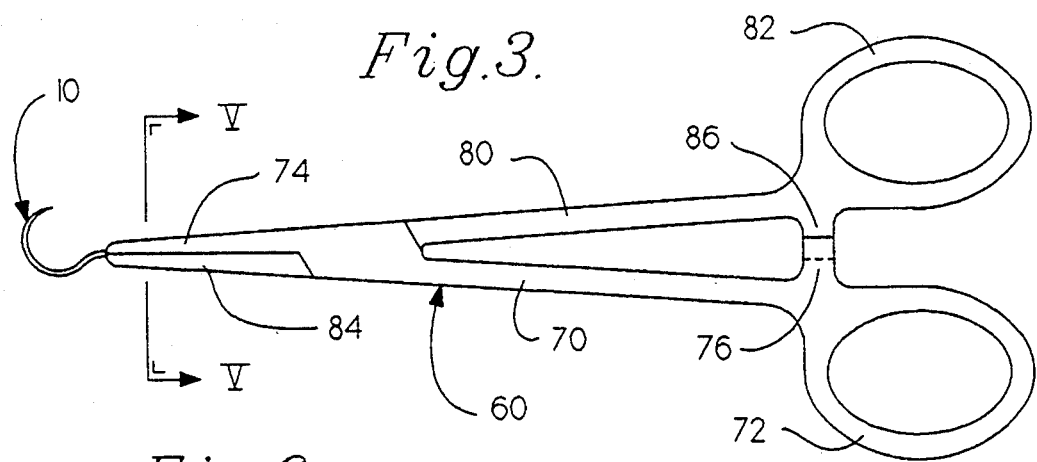
FIG. 3 is a side elevational view of the surgical needle of FIG. 1 as held in an optional improved needle holder according to a preferred embodiment of the present invention.

Referring to the FIGS. 1 and 2, the needle 10 of the present invention includes an arcuate body segment 20, an arcuate neck segment 30 and a straight shank segment 40. As shown in FIG. 2, the needle has an overall length H which is preferably in the range of approximately 14 millimeters and an overall width W of approximately 10 millimeters. The needle is preferably formed of wire having a circular cross sectional diameter of approximately 1 millimeter. As used herein, the terms "approximately" or "substantially" shall be construed to mean plus or minus 15% of the distance or angle used in conjunction with such term.

Main body segment 20 has a central base portion 24 located at an intersection of an extension 44 (shown in chain line) of the centerline of shank 40. Main body segment 20 terminates at a sharp pointed end at 22. Main body segment 20 preferably has an internal radius of curvature R between approximately 4 millimeters and 5 millimeters with a preferred radius distance of 4.5 millimeters.

The main body segment 20 extends for an arcuate distance $\alpha$ which a minimum arcuate length of approximately 180 degrees, a maximum of 230 degrees and a preferred arcuate distance of approximately 215 degrees. As best shown in FIG. 1, the pointed end portion of the body tapers gradually to a sharp point over a substantial arcuate distance $\pi$, which in the preferred embodiment of the invention is approximately 90 degrees.

It is noted that the needle is designed so that an extension line 44 (shown in chain line) of a centerline of the shank 40 intersects an extension line 26 (also shown in chain line) which passes through the sharp point 22 and center point C at an angle $\delta$ which is between approximately 45 degrees and 90 degrees with a preferred angle of approximately 80 degrees. This angle is important so as to allow for insertion of the needle into a deep narrow wound by pushing the center portion 24 downwardly without having the point 22 puncture the facia at an undesired location. Further, such angle also allows for a relatively minor torquing motion of the deeply inserted needle to result in a puncture of the facia at the desired location.

The neck segment 30 of the surgical needle bends in a convex fashion relative to the concave bend of the body segment. The neck portion preferably has a gently curving arcuate shape and extends for an arcuate distance of β degrees. Preferably, angle β has a value of approximately 45 degrees.

The shank of the needle 40 is formed to be straight and has a distance d which at a maximum is approximately 4 millimeters, at a minimum approximately 2.5 millimeters and a preferred distance of approximately 3 millimeters. Preferably, shank length d is not substantially greater than the internal radius R of main body segment 20. Uppermost end 42 of shank segment 40 is adapted to receive and secure a length of suture material 50 by means well known in the art.

As shown in FIG. 3–6, the surgical needle of the present invention is optionally held by a specially formed needle holder 60. Needle holder 60 includes two pivoting arms 70 and 80 which provide, respectively: handle portions 72 and 82; needle nose portions 74 and 84; and gripping portions 76 and 86, all of which features are well known in the art in standard surgical needle holders.

Figure 4:
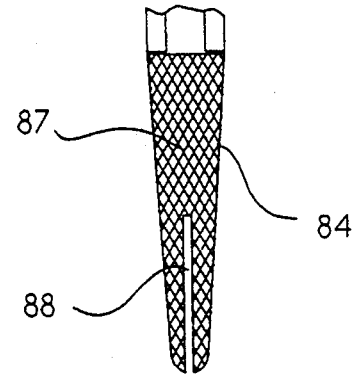
FIG. 4 is a top plan view of the needle tip of one jaw portion of the needle holder of FIG. 3 showing a groove in the gripping surface thereof.
Figure 5:
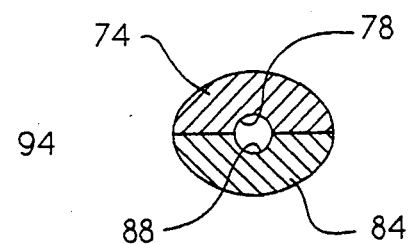
FIG. 5 is a cross sectional view of the needle holder (needle not shown) taken on the line V—V of FIG. 3.

As shown in FIGS. 4 and 5, however, a groove 78 and 88 is provided respectively into the gripping faces 77 (not shown) and 87 of the needle nose ends 74 and 84. The grooves 78 and 88 are formed and sized to receive and securely hold and lock in place the surgical needle 10 in a perpendicular orientation as best shown in FIG. 3. These grooves are preferably approximately 10 millimeters in length and have a width slightly less than the diameter of the shank of the needle which the groove is adapted to receive. The grooves 78 and 88 aid in securing the needle 10 in a desired orientation in the needle holders and prevent undesirable twisting of the needle during the suturing process.

Figure 6:
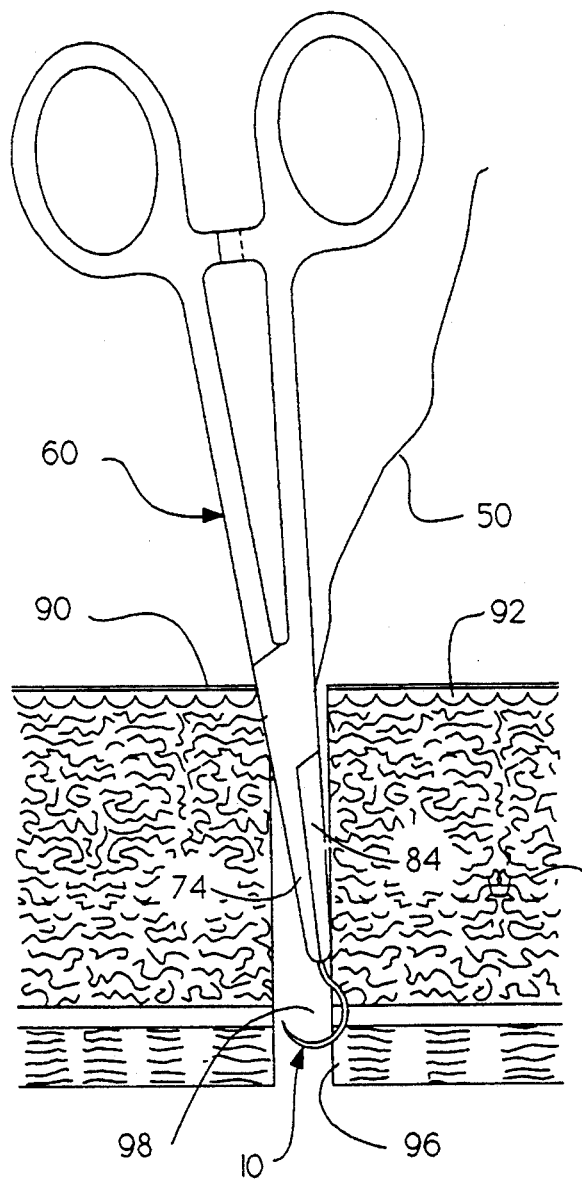
FIG. 6 is a side elevational view of the needle holder and needle of FIG. 3 as inserted deeply into a subcutaneous layer of abdominal tissue.

Referring to FIG. 6, in use the specially made needle 10 is loaded perpendicularly into the grooved tip 74, 84 of the needle holder 60 and inserted deeply through the epidermis 90, dermis 92 and subcutaneous fatty layer 94, touching the fascia 96 with the curved body segment of the needle. The needle 10 is then angled and the fascia is sutured with suture material 50 on one side and the needle is brought through the fascial defect 98. The needle tip 22 is then grasped with a conventional hemostat (not shown) by an assistant. The needle is then brought out through the abdominal wall. Needle holder 60 is reloaded in the same fashion and the opposite site of fascia is sutured through the fascial defect 98. The needle is then brought out from the wound and the wound is closed. Pneumoperitoneum is re-established to assure undesirable tissue is caught during the procedure. The same needle 10 is then loaded with the same needle holder 60 on a right angle position (transversely to the position shown in FIGS. 3 and 6) and the fascia is sutured on the shallow umbilical port using the conventional method.

It is noted that the conventional needles of the prior art, such as the half circle, semicircle, the quarter circle, ski-type, and fish-hook type needles are loaded by a needle holder at a right angle position to suture the surface of a wide open wound. However, it is impossible to use these types of needles to reach deeply lying fascia during laparascopic surgery because the needles cannot be held sturdily enough to prevent movement of the needle during deep insertion. In contrast, the small, sickle-type needle of the present invention has a short, stable shank which enables it to be easily grasped and stabilized by the special, grooved needle holder tip. Further, the needles unique shape and curvature makes it easy to drive and encircle the deeply located fascia through a narrow puncture wound.

While I have shown and described the presently preferred embodiment of my invention, the invention is not limited thereto and may be otherwise variously practiced within the scope of the following claims.

I claim:

1. A surgical needle for fascial suturing comprising:
   a) a solid arcuate body segment curving in a concave manner, said body segment having an internal radius of curvature around a center point, and said body segment terminating at a sharp point;
   b) a straight shank segment having a suture attached at a terminal end thereof, said shank segment having a length not substantially greater than said internal radius of curvature of said body segment; and
   c) a solid neck segment positioned intermediate and connecting together said body segment and said shank segment, said neck segment curving in a convex manner relative to said body segment whereby said shank segment is attached to said body segment at an angle such that an extension of an axial centerline of said shank segment intersects said arcuate body segment of the needle in a central third portion of said body segment.

2. A surgical needle according to claim 1 wherein said extension of said centerline of said shank segment intersects an extension of a line passing through said center point and sharp point at an angle between approximately 45 degrees and 90 degrees.

3. A surgical needle according to claim 1 wherein said extension of said centerline of said shank segment intersects an extension of a line passing through said center point and sharp point at an angle of approximately 80 degrees.

4. A surgical needle according to claim 1 wherein said body segment extends an arcuate distance of between approximately 180 degrees to 230 degrees.

5. A surgical needle according to claim 1 wherein said body segment extends an arcuate distance of approximately 215 degrees.

6. A surgical needle according to claim 1 wherein said internal radius of curvature is between approximately 4 millimeters and 5 millimeters in length.

7. A surgical needle according to claim 1 wherein said internal radius of curvature is approximately 4.5 millimeters in length.

8. A surgical needle according to claim 1 wherein said surgical needle has an overall length of approximately 14 millimeters.

9. A surgical needle according to claim 1 wherein said surgical needle has an overall width of approximately 10 millimeters.

10. A surgical needle according to claim 1 wherein said surgical needle is formed of wire of generally circular cross section, said wire having a diameter of approximately 1 millimeter.

11. A surgical needle according to claim 1 wherein said shank segment is between approximately 2.5 millimeters and 4 millimeters in length.

12. A surgical needle according to claim 1 wherein said shank segment is approximately 3 millimeters in length.

13. A surgical needle for fascial suturing comprising:
a) an arcuate body segment curving in a concave manner, said body segment having an internal radius of curvature around a center point, and said body segment terminating at a sharp point, wherein said sharp point end of said body segment is tapered and tapers gradually from the cross sectional diameter of a nontapered portion of the body to a sharp point over an arcuate distance of approximately 90 degrees;
b) a straight shank segment having a suture attached at a terminal end thereof, said shank segment having a length not substantially greater than said internal radius of curvature of said body segment; and
c) a neck segment positioned intermediate and connecting together said body segment and said shank segment, said neck segment curving in a convex manner relative to said body segment whereby said shank segment is attached to said body segment at an angle such that an extension of an axial centerline of said shank segment intersects said arcuate body segment of the needle in a central portion of said body segment.

14. A surgical needle apparatus for fascial suturing comprising:
a) a surgical needle having: an arcuate body segment curving in a concave manner, said body segment having an internal radius of curvature around a center point, and said body segment having an end terminating at a sharp point; a straight shank segment having a suture attached at a terminal end thereof; and a neck segment positioned intermediate and connecting together said body segment and said shank segment, said neck segment curving in a convex manner relative to said body segment whereby said shank segment is attached to said body segment at an angle such that an extension of an axial centerline of said shank segment intersects said arcuate body segment of the needle; and
b) a needle holding means in the form of surgical needle holders having a pair of needle nosed gripping faces at one end movable between a first open position and a second closed position for gripping said shank segment of said surgical needle, each of said gripping faces having a longitudinal groove formed therein to receive a position, said shank segment in axial alignment with said grooves.

15. A surgical needle apparatus according to claim 14 wherein said shank segment has a cross sectional diameter greater than the width of said grooves.

16. A surgical needle apparatus according to claim 14 wherein said grooves have an axial length of approximately 10 millimeters.

* * * * *